United States Patent
Li et al.

(10) Patent No.: US 12,112,027 B2
(45) Date of Patent: Oct. 8, 2024

(54) SYSTEM AND METHOD FOR DISPLAYING HIGH-RESOLUTION LIVER CANCER PATHOLOGICAL IMAGE BASED ON IMAGE PYRAMID

(71) Applicant: ZHEJIANG LAB, Zhejiang (CN)

(72) Inventors: Jingsong Li, Hangzhou (CN); Feixiang Song, Hangzhou (CN); Bo Zhang, Hangzhou (CN); Tianshu Zhou, Hangzhou (CN); Yu Tian, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/363,679

(22) Filed: Aug. 1, 2023

(65) Prior Publication Data

US 2024/0168618 A1    May 23, 2024

(30) Foreign Application Priority Data

Nov. 4, 2022    (CN) .......................... 202211375032.0

(51) Int. Cl.
*G06F 3/04845* (2022.01)
*G06F 3/0354* (2013.01)
(Continued)

(52) U.S. Cl.
CPC ...... *G06F 3/04845* (2013.01); *G06F 3/03543* (2013.01); *G06F 3/0487* (2013.01);
(Continued)

(58) Field of Classification Search
CPC ............. G06F 3/04845; G06F 3/03543; G06F 3/0487; G06T 3/40; G06T 5/70;
(Continued)

(56) References Cited

U.S. PATENT DOCUMENTS 9,158,973 B1 * 10/2015 Garg .......................... G06T 7/90
2013/0305138 A1    11/2013 Gicovate
(Continued)

FOREIGN PATENT DOCUMENTS

CN       1928871 A      3/2007
CN    103345495 A     10/2013
(Continued)

OTHER PUBLICATIONS

Notice of Allowance(CN202211375032.0); Date of Mailing: Feb. 28, 2023.
(Continued)

*Primary Examiner* — David D Davis
(74) *Attorney, Agent, or Firm* — W&G Law Group (57) ABSTRACT

Provided are a system and a method for displaying a high-resolution liver cancer pathological image based on an image pyramid. The system includes a data source processing module and an image display module. The data source processing module is configured to acquire original images in various states, process the original images, acquire an image pyramid, name image blocks in the image pyramid, and store the image blocks in a folder set for the image pyramid in a server. The image display module is configured to acquire the image blocks in the folder set for the image pyramid in the server, acquire the image blocks according to a user's request, and splice and display the image blocks in an image display area. For the spliced image blocks, enlargement, reduction and translation operations are supported.

3 Claims, 9 Drawing Sheets (51) Int. Cl.
   *G06F 3/0487*    (2013.01)
   *G06T 3/40*      (2024.01)
   *G06T 5/70*      (2024.01)
   *G06T 7/11*      (2017.01)
   *G16H 30/20*     (2018.01)

(52) U.S. Cl.
   CPC ................. *G06T 3/40* (2013.01); *G06T 5/70* (2024.01); *G06T 7/11* (2017.01); *G16H 30/20* (2018.01); *G06T 2200/24* (2013.01); *G06T 2207/20016* (2013.01); *G06T 2207/20021* (2013.01); *G06T 2207/20092* (2013.01); *G06T 2207/30056* (2013.01)

(58) Field of Classification Search
   CPC .................. G06T 7/11; G06T 2200/24; G06T 2207/20016; G06T 2207/20021; G06T 2207/20092; G06T 2207/30056; G16H 30/20
   See application file for complete search history.

(56) References Cited

U.S. PATENT DOCUMENTS

| | | | |
|---|---|---|---|
| 2014/0126841 A1 | 5/2014 | Wang et al. | |
| 2014/0306992 A1* | 10/2014 | Tsujimoto | G16H 70/60 345/632 |
| 2015/0195430 A1* | 7/2015 | Wadhwa | H04N 5/144 348/581 |
| 2015/0324660 A1* | 11/2015 | Stein | G06V 10/60 382/164 |
| 2015/0324661 A1* | 11/2015 | Smith | G06V 10/50 382/164 |

FOREIGN PATENT DOCUMENTS

| | | |
|---|---|---|
| CN | 104134214 A | 11/2014 |
| CN | 105989130 A | 10/2016 |
| CN | 107679164 A | 2/2018 |
| CN | 109657172 A | 4/2019 |
| CN | 112164066 A | 1/2021 |
| CN | 114022388 A | 2/2022 |
| CN | 115206498 A | 10/2022 |
| EP | 3839885 A1 | 6/2021 |

OTHER PUBLICATIONS

First Office Action(CN202211375032.0); Date of Mailing: Dec. 21, 2022.
A-large-image-processing-and-display-method-based-on-GD2-and-Canvas Mechanical translation.

* cited by examiner

|  | $0^{th}$ column | $(m-1)^{th}$ column | $m^{th}$ column |
|---|---|---|---|
| $0^{th}$ row | Size: a × a<br>Name: 0_0 | ...... | Size: a × a<br>Name: 0_m-1 | Size: (Width-m × a) × a<br>Name: 0_m |
| ...... | ...... | ...... | ...... | ...... |
| $(n-1)^{th}$ row | Size: a × a<br>Name: n-1_0 | ...... | Size: a × a<br>Name: n-1_m-1 | Size: (Width-m × a) × a<br>Name: n-1_m |
| $n^{th}$ row | Size: a × (Height - n × a)<br>Name: n_0 | ...... | Size: a × (Height - n × a)<br>Name: n_m-1 | Size: (Width-m × a) × (Height - n × a)<br>Name: n_m |

FIG. 11

SYSTEM AND METHOD FOR DISPLAYING HIGH-RESOLUTION LIVER CANCER PATHOLOGICAL IMAGE BASED ON IMAGE PYRAMID

CROSS-REFERENCE TO RELATED APPLICATIONS

The present application claims priority to Chinese Patent Application No. 202211375032.0, filed on Nov. 4, 2022, the content of which is incorporated herein by reference in its entirety.

TECHNICAL FIELD

The present application relates to the technical field of image display, in particular to a method and a system for displating a high-resolution liver cancer pathological image based on an image pyramid.

BACKGROUND

Image resolution refers to the amount of information stored in an image, that is, how many pixels there are in an image per inch. Resolution determines the fineness of image details. Generally, the higher the resolution of an image, the more pixels it contains, the clearer the image, and the more storage space it takes up. With the improvement of mobile phone, computer hardware and network bandwidth, more and more high-definition images can be seen on PC or a mobile phone browser, but it is still restricted by hardware, software, network, and other factors.

A pathological image is a high-resolution image taken under a scanner after a tissue is carried on a glass slide. Pathological images can help doctors diagnose patients. For example, by pathological images of liver cancer, the specific situation of liver cancer cells can be seen. The size of the pathological images is usually on the order of $10^5 \times 10^5$. A gray-scale image with $10^5 \times 10^5$ pixels takes up about 9.31 GB of memory space without compression, which will bring a devastating blow to the performance of Web browsers.

In fact, in order to prevent the browser from crashing due to lack of memory, when the image size exceeds a certain limit, the image will be downsampled and displayed at a fraction of the original resolution. For example, for a Google Chrome browser on the PC side, the upper limit of the image size that can be displayed normally is 16384×16384 pixels; however, the restrictions of mobile phone browsers are even smaller. For example, the Safari browser of iOS10 has an upper limit of 4096×4096 pixels. Obviously, $10^5 \times 10^5$ far exceeds these limits.

At present, there are three mainstream methods to display super-large pixel images on the browser.

The first method is to compress the super-large pixel image to the size that can be displayed by the browser. However, this method is not suitable for pathological images, which need to pay attention to the details of the image.

The second method is a cutting and splicing method. According to the screen resolution and display area, the original image is cut into several images that can be displayed correctly by the browser, and then these small images are spliced in the display area of the browser in sequence. This method can show the details of the image to a certain extent, but when the pixels of the image are too high and the display area of the browser is too small, only part of the image or the global image with lower resolution can be displayed. If part of the image is to be shown, it is necessary to drag and translate the image to be viewed, and the area including the desired details cannot be quickly located. When the image is large, viewing the target image area is time-consuming due to the limited mouse drag distance.

The third method is a depth scaling method. The original image is continuously downsampled to generate a series of approximate images, which together with the original image form an image pyramid. The original image and these approximate images are named according to certain naming rules and stored on the server, and then the browser obtains image blocks with corresponding resolutions and corresponding areas according to the display area and level. OpenSeadragon (open source address: https://github.com/openseadragon/openseadragon), a tool with depth zoom function, can be used to achieve this operation. However, OpenSeadragon has two shortcomings: 1) it only supports synchronous acquisition of image blocks, which is a huge challenge to the browser memory; 2) only one image can be processed and displayed at a time, and when multi-state images need to be displayed at the same time, this tool cannot meet the requirements.

Therefore, a method and a system for displating a high-resolution liver cancer pathological image based on an image pyramid are proposed.

SUMMARY

The present application aims to provide a method and a system for displaying a high-resolution liver cancer pathological image based on an image pyramid, which solve the following problems in the prior art: how to quickly and elegantly display high-resolution liver cancer pathological images to users, how to enable users to quickly locate and enlarge the detailed images of the areas they want to observe, thus bringing better user experience, how to acquire the image blocks in an asynchronous way, which can effectively reduce the waiting time of users for image display, improve performance and improve user experience, and how to provide the function of supporting multi-state image display of high-resolution liver cancer pathological images.

The present application adopts the following technical solutions.

A system for displaying a high-resolution liver cancer pathological image based on an image pyramid includes a data source processing module and an image display module.

The data source processing module is configured for acquiring original images in various states, processing the original images, acquiring an image pyramid, naming image blocks in the image pyramid, and storing the image blocks in a folder set for the image pyramid in a corresponding server.

The image display module is configured for acquiring the image blocks in the folder set for the image pyramid in the server, zooming in, zooming out and translating the image blocks according to a user's request, and splicing the image blocks and displaying the image blocks in an image display area.

Further, the data source processing module specifically includes: a data source processing unit and an image block processing unit.

The data source processing unit is configured for acquiring the original images in various states from an original image database, setting a size threshold, calculating a size of the original images, calculating a maximum number of levels of the image pyramid according to the size threshold and the size of the original images, and calculating an image cutting size from the maximum number of levels of the image pyramid.

The image block processing unit is configured for pre-processing the original images and cutting the preprocessed original images according to the image cutting size to obtain a plurality of image blocks. Each level of the image blocks together forms an image pyramid, and each image block is named and stored in the folder set for the image pyramid in the corresponding server.

Further, a specific process of the data source processing unit is as follows.

The original images in various states are acquired from an original image database. The size, including a width of the original images and a height of the original images, of the original images is calculated, and the size threshold is set.

When the width of the original images is less than or equal to the height of the original images, the original images are downsampled. When the width of the original images reaches the size threshold, the downsampling is stopped. The number of times of downsampling is calculated, which corresponds to the maximum number of levels of the image pyramid, and the image cutting size is calculated according to the number of times of downsampling.

When the width of the original images is larger than the height of the original images, the original images are downsampled. When the height of the original images reaches the size threshold, the downsampling is stopped. The number of times of downsampling is calculated, which corresponds to the maximum number of levels of the image pyramid, and the image cutting size is calculated according to the number of times of downsampling.

Further, a specific process of the image block processing unit is as follows.

Step S1, Gaussian blur processing is performed on the original image as a target image to obtain a filtered image subjected to Gaussian blur.

Step S2, the filtered image is downsampled to obtain an approximate image.

Step S3, the target image is cut according to the image cutting size to obtain a plurality of image blocks.

Step S4, an image pyramid is formed by each level of the image blocks, and each image block is named and stored in the folder set for the image pyramid in the corresponding server.

Step S5, when a width of the approximate image is larger than a width of the image cutting size, the approximate image is taken as the target image in step S1 and steps S1-S5 are traversed. Otherwise, a last approximate image obtained in step S2 is cut according to the image cutting size, each cut image block is named and stored in the folder set for the image pyramid in the corresponding server.

Further, each image block in the image block processing unit is named according to a character string spliced by underlining with a row number and a column number in the image pyramid, and the image block is stored in the folder set for the image pyramid in the corresponding server.

Further, the image display module includes a client and a server.

The client is configured for initiating a request for obtaining basic information of an image to a server and simultaneously monitoring user mouse events, asynchronously requesting for image blocks to be loaded to the server according to a user's operation, and splicing the obtained image blocks and displaying them in the image display area of a browser. In some embodiments, the requested input parameters include a state of the liver cancer pathological image where the image blocks to be obtained are located, a level where the image blocks are located, a row number and a column number.

The server is configured for obtaining information including the size of the original images in each state, the maximum number of levels of the image pyramid, the image block and/or the image cutting size from the data source processing unit, responding the information to the client, obtaining responded image blocks according to the state of the liver cancer pathological image where the image block is located, the level, the row number and the column number, and returning the responded image blocks to the client.

Further, the monitored user mouse events specifically includes an operation of clicking mouse or scrolling down mouse by a user, an operation of upward scrolling mouse by a user, and a translation operation by a user.

When the user clicks or scrolls down the mouse, if the current image pyramid is at the bottom, the displayed image remains unchanged. Otherwise, the operation is used for carrying out a zooming-in operation, and displaying a corresponding image block of an approximate image in a lower level with an area, as a center, where the mouse is clicked or scrolled.

When the user scrolls up the mouse, if the current image pyramid is at the top level, the displayed image remains unchanged. Otherwise, the operation is used for carrying out a zooming-out operation, and displaying a corresponding image block of an approximate image an upper level with an area where the mouse is scrolled as a center.

When the user performs the translation operation, if the current image pyramid is at an edge or cannot be moved anymore, the displayed image remains changed. Otherwise, the operation is used for continuing the translation operation, and acquiring the image blocks to be displayed as needed, and then splicing and displaying.

Further, the zooming-in operation includes the following steps: obtaining the row number and column number of the image block where a mouse action position is located in a current level according to a coordinate of the mouse action position of the current level in the image pyramid, and obtaining the row number and column number of the corresponding image block in a lower level through the corresponding relationship between the image block in the current level and the image block in the lower level, so as to obtain the corresponding requested input parameters.

The zooming-out operation includes the following steps: acquiring the row number and column numb of the image block where the mouse action position is located in the current level according to the coordinate of the mouse action position of the current level in the image pyramid, and acquiring the row number and column number of the image block corresponding to the upper level through the corresponding relationship between the image block in the current level and the image block in the upper level, so as to obtain the corresponding requested input parameters.

The translation operation includes the following steps: setting a variable S, which is used for marking and storing the requested image blocks, wherein the storage content is the level, row number and column number of the image block; circularly traversing a row range and a column range of the image blocks in the display area at the client-side respectively, and combining the row number and column number to obtain the parameters of the image block to be requested, wherein when the image block has been marked by the variable S, there is no need to repeat the request; otherwise, requesting for the image block from the server-side.

Further, in the translation operation, when the image is translated to the right edge, it cannot be moved to the left anymore. When the image is translated to the left edge, it cannot be moved to the right anymore. When the image is translated to the upper edge, it cannot be moved down anymore. When the image is translated to the lower edge, it cannot be moved up anymore.

The present application further provides a method for displaying a high-resolution liver cancer pathological image based on an image pyramid, and the method incudes the following steps.

Step S101, original images in various states are acquired and processed by a data source processing module to acquire an image pyramid, and the image blocks in the image pyramid are named and stored in a folder set for the image pyramid in a corresponding server;

Step S102, the image blocks in the folder set for the image pyramid in the server are required by an image display module, the image blocks are acquired according to a user's request for zooming in, zooming out and translating, and the image blocks are spliced and displayed in an image display area.

The present application has the following advantages: the present application provides a method and a system for displaying a high-resolution liver cancer pathological image based on an image pyramid on a Web browser. According to a complete method for image enlargement, reduction and translation designed for the client of an image display module, the high-resolution liver cancer pathological image can be quickly and elegantly displayed to users, and the users can quickly locate and enlarge the detailed image of the desired area. A way to acquire image blocks asynchronously is innovatively provided, which can effectively reduce the waiting time of users for image display and improve the user experience. At the same time, multi-state display of high-resolution liver cancer pathological images are supported, for example liver cancer pathological images of the two states, i.e., the original state and the state marked with the tissue classification result, are displayed simultaneously.

DESCRIPTION OF EMBODIMENTS

The following description of at least one exemplary embodiment is merely illustrative in nature and is in no way intended to limit the present application, its present application or uses. Based on the embodiments in the present application, all other embodiments obtained by those skilled in the art without creative work shall belong to the scope of protection of the present application.

Figure 1:
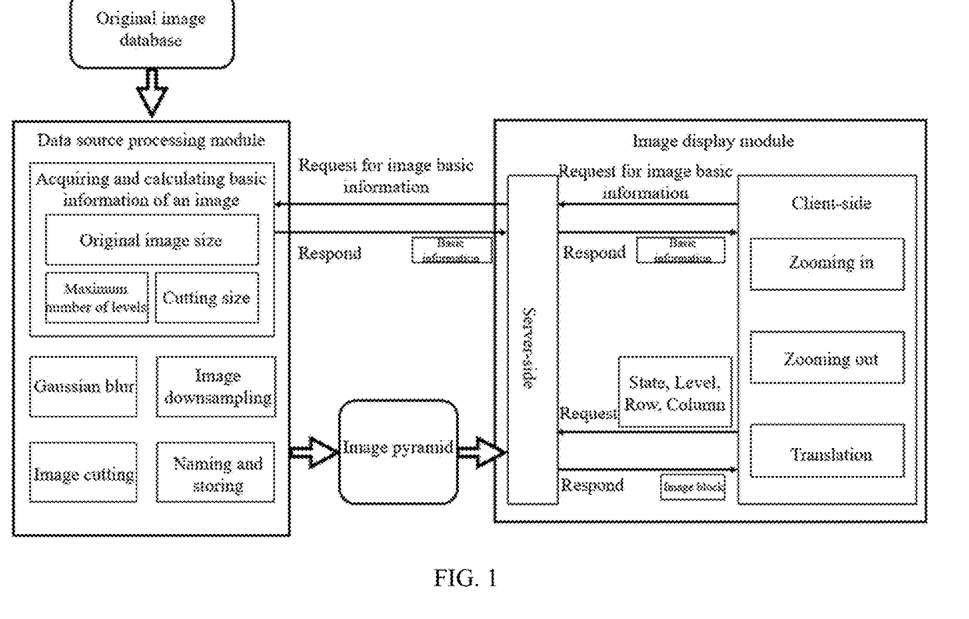
FIG. 1 is an overall frame diagram of a system for displaying a high-resolution liver cancer pathological image based on an image pyramid according to the present application.

Referring to FIG. 1, a system for displaying a high-resolution liver cancer pathological image based on an image pyramid includes a data source processing module, an image display module.

The data source processing module is used for acquiring original images in various states, processing the original images, acquiring an image pyramid, naming image blocks in the image pyramid and storing the image blocks in a folder set for the image pyramid in a corresponding server;

the image pyramid is an image collection composed of several sub-images with different resolutions of an image, which is generated by continuously downsampling an image;

the smallest image may only have one pixel; the simplest image pyramid can be obtained by constantly deleting even rows and even columns of images.

Figure 2:
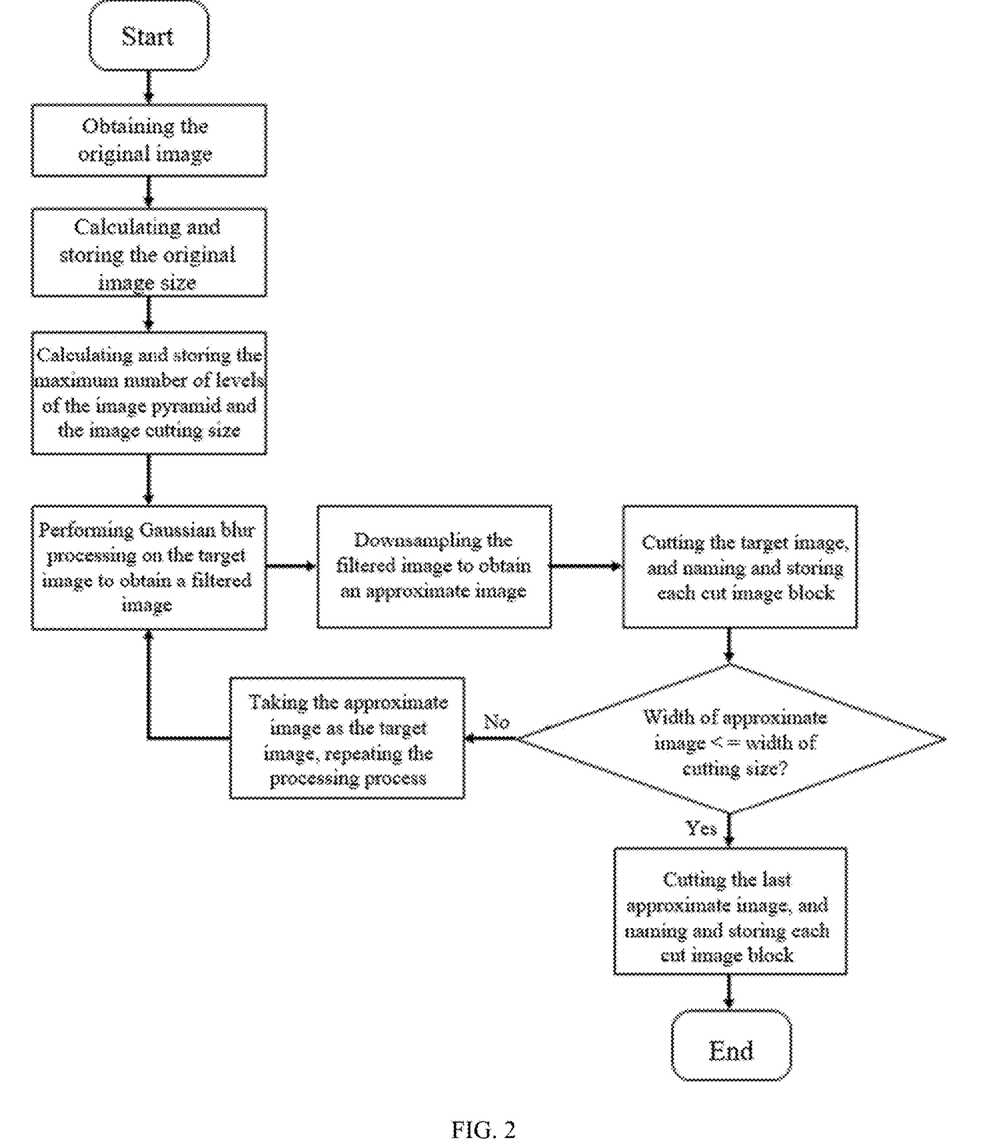
FIG. 2 is a functional flow chart of a data source processing unit according to the present application.

The data source processing module specifically includes a data source processing unit and an image block processing unit;

the data source processing unit is used for acquiring the original images in various states from an original image database, setting a size threshold, calculating a size of the original images, calculating a maximum number of levels of the image pyramid according to the size threshold and the size of the original images, and calculating an image cutting size from the maximum number of levels of the image pyramid;

see FIG. 2, specific process of the data source processing unit is as follows:

the original images in various states are acquired from an original image database, the size, comprising a width of the original images and a height of the original images, of the original images is calculated, and the size threshold is set;

a default size threshold is set to 500×500, and it is assumed that the width of the original images is Width and the height is Height;

when the width of the original images is less than or equal to the height of the original images, the original images are downsampled until the width of the original images reaches the size threshold, the downsampling is stopped, the number of times of downsampling is calculated, that is, the maximum number of levels of the corresponding image pyramid, and the image cutting size is calculated from the number of times of downsampling;

the images are continuously downsampled until the width reaches the size threshold, and accordingly a number of times of downsampling i shall satisfy $$\frac{\text{Width}}{2^i} \leq 500, i \in N, i \geq \log_2 \frac{\text{Width}}{500}, i \in N,$$

is calculated, and a minimum value that meets the condition is taken to obtain the number of times of downsampling, that is, the maximum number of levels of the image pyramid, and then the calculated i is substituted into to $$\left\lceil \frac{\text{Width}}{2^i} \right\rceil$$

obtain the image cutting size $$\left\lceil \frac{\text{Width}}{2^i} \right\rceil \times \left\lceil \frac{\text{Width}}{2^i} \right\rceil;$$

when the width of the original images is larger than the height of the original images, the original images are downsampled until the height of the original images reaches the size threshold, the downsampling is stopped, the number of times of downsampling is calculated, that is, the maximum number of levels of the corresponding image pyramid, and the image cutting size is calculated from the number of times of downsampling;

the images are continuously downsampled until the height reaches the size threshold, and accordingly a number of times of downsampling i shall satisfy $$\frac{\text{Height}}{2^i} \leq 500, i \in N, i \geq \log_2 \frac{\text{Height}}{500}, i \in N,$$

is calculated, and a minimum value that meets the condition is taken to obtain the number of times of downsampling, that is, the maximum number of levels of the image pyramid, and then the calculated i is substituted into $$\left\lceil \frac{\text{Height}}{2^i} \right\rceil$$

to obtain the image cutting size $$\left\lceil \frac{\text{Height}}{2^i} \right\rceil \times \left\lceil \frac{\text{Height}}{2^i} \right\rceil.$$

the image block processing unit is used for preprocessing the original images and cutting the preprocessed original images according to the image cutting size to obtain a plurality of image blocks; each level of the image blocks together forms an image pyramid, and each image block is named and stored in the folder set for the image pyramid in the corresponding server.

Figure 3:
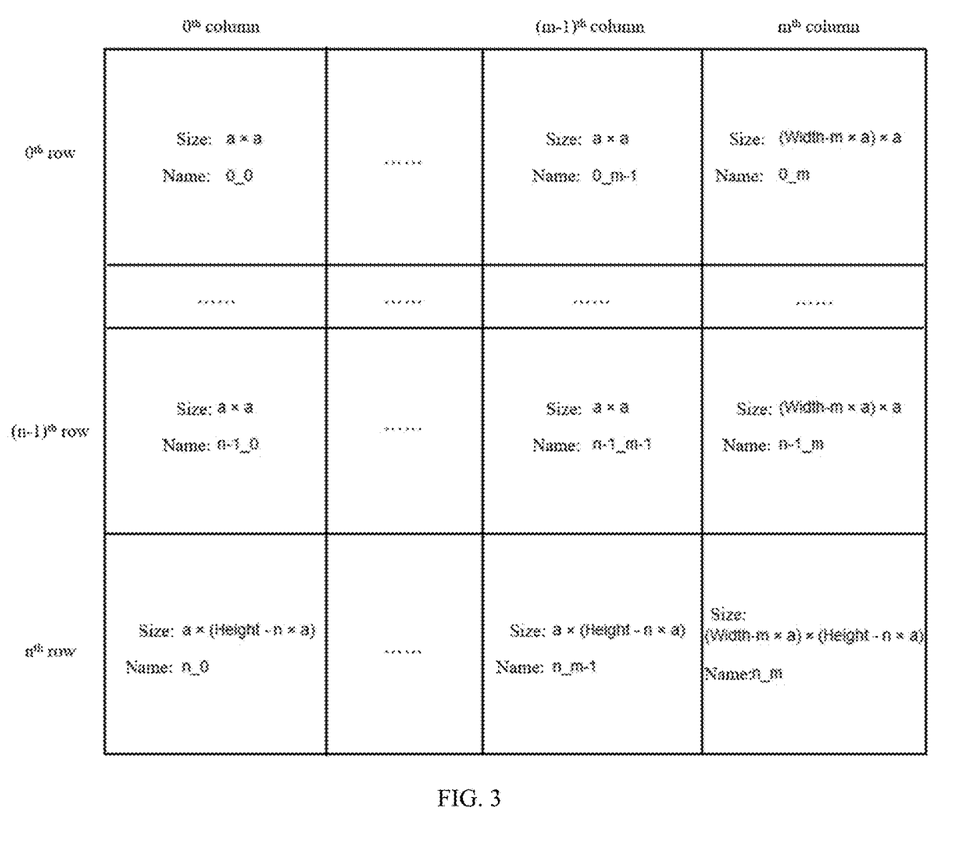
FIG. 3 is a schematic diagram of image block segmentation and naming according to the present application.

Referring to FIG. 3, it is known that the maximum number of levels of the image pyramid is N and the cutting size is a×a, where N and a are positive integers greater than 0; the image of the i $(0 \leq i \leq N)^{th}$ level with the size of Width×Height can be cut into four image blocks with different sizes, including: m×n image blocks with a size of a×a, n image blocks with a size of (Width−m×a)×a, m image blocks with a size of a×(Height−n×a) and one image block with a size of (Width−m×a)×(Height−n×a), where n, m∈N, n and m are the row number and column number of the image block, respectively, and the image block is named as n_m with a character string by spicing the row number and column number with an underline. All the image blocks in the i$^{th}$ level will be stored in the folder named i, which is the target storage space specially opened for the image pyramid on the server.

The specific process of the image block processing unit is as follows.

Step S1, Gaussian blur processing is performed on the original image as a target image to obtain a filtered image subjected to Gaussian blur.

Step S2, the filtered image is downsampled to obtain an approximate image.

Step S3, the target image is cut according to the image cutting size to obtain a plurality of image blocks.

Step S4, an image pyramid is formed by each level of the image blocks, and each image block is named and stored in the folder set for the image pyramid in the corresponding server.

Step S5, when a width of the approximate image is larger than a width of the image cutting size, the approximate image is taken as the target image in step S1 and steps S1-S5 are traversed. Otherwise, a last approximate image obtained in step S2 is cut according to the image cutting size, each cut image block is named and stored in the folder set for the image pyramid in the corresponding server.

Each image block in the image block processing unit is named as n_m according to a character string obtained by splicing a row number n and a column number m in the image pyramid with an underline, and the image block is stored in the folder set for the image pyramid in the corresponding server.

The image display module is used for acquiring the image blocks in the folder set for the image pyramid in the server, zooming in, zooming out and translating the image blocks according to a user's request, and splicing the image blocks and displaying the image blocks in an image display area.

Figure 4:
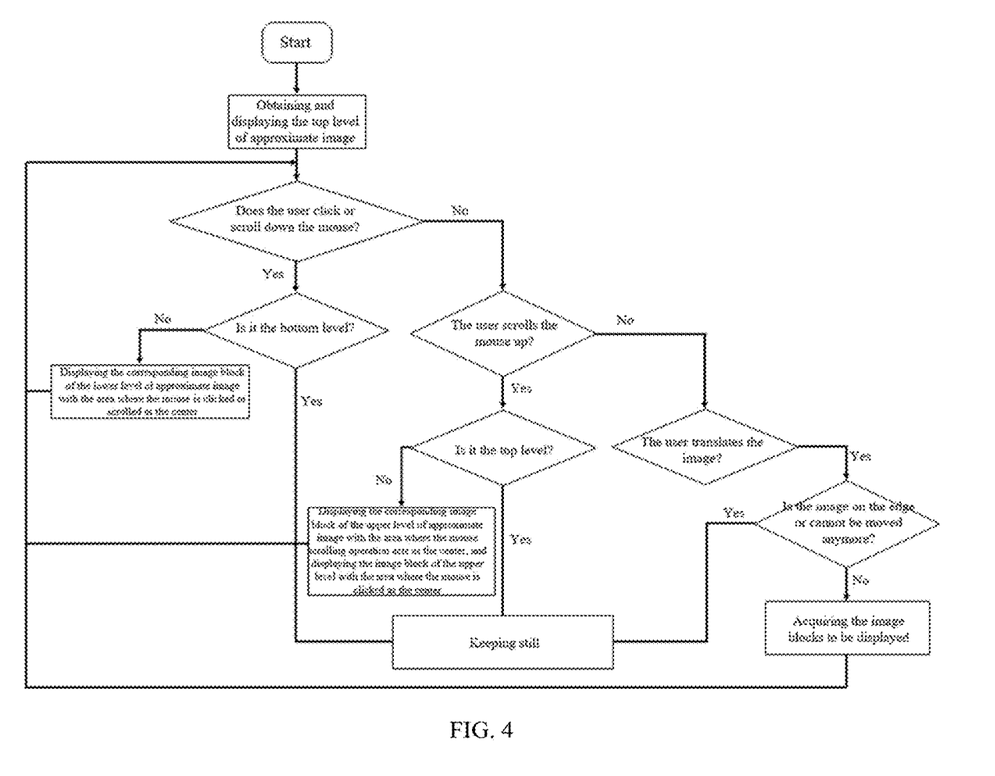
FIG. 4 is a functional flowchart of an image display module according to the present application.

As shown in FIG. 4, the image display module includes a client and a server.

The client is used for initiating a request for obtaining basic information of an image to the server and simultaneously monitoring user mouse events, asynchronously requesting for image blocks to be loaded to the server according to a user's operation, and splicing the obtained image blocks and displaying them in the image display area of a browser. In some embodiments, the requested input parameters include a state of the liver cancer pathological image where the image blocks to be obtained are located, a level where the image blocks are located, a row number and a column number.

The monitored user mouse events specifically includes an operation of clicking mouse or scrolling down mouse by a user, an operation of upward scrolling mouse by a user and a translation operation by a user.

When the user clicks or scrolls down the mouse, if the current image pyramid is at the bottom (i.e., the 0$^{th}$ level), the displayed image remains unchanged. Otherwise, the operation is used for carrying out a zooming-in operation, and displaying a corresponding image block of an approximate image in a lower level with an area where the mouse is clicked or scrolled as a center.

The zooming-in operation includes the following steps: obtaining the row number and column number of the image block where a mouse action position is located in a current level according to a coordinate of the mouse action position of the current level in the image pyramid, and obtaining the row number and column number of the corresponding image block in a lower level through the corresponding relationship between the image block in the current level and the image block in the lower level, so as to obtain the corresponding requested input parameters.

Assuming that the current level is p, the coordinate of the mouse action position is (i,j), the row of the corresponding image block is $$\left\lfloor \frac{j}{a} \right\rfloor,$$

and the column thereof is $$\left\lfloor \frac{i}{a} \right\rfloor;$$

there are four image blocks corresponding to the lower level, and pairs of the row number and column number thereof are $$\left[2\times\left\lfloor \frac{j}{a} \right\rfloor, 2\times\left\lfloor \frac{i}{a} \right\rfloor\right], \left[2\times\left\lfloor \frac{j}{a} \right\rfloor, 2\times\left\lfloor \frac{i}{a} \right\rfloor+1\right], \left[2\times\left\lfloor \frac{j}{a} \right\rfloor+1, 2\times\left\lfloor \frac{i}{a} \right\rfloor\right] \text{ and } \left[2\times\left\lfloor \frac{j}{a} \right\rfloor+1, 2\times\left\lfloor \frac{i}{a} \right\rfloor+1\right]$$

respectively, then the client-side needs to request for the addresses of these four image blocks from the server-side, and the requested input parameters are as follows.

1) level p, row:

$$2\times\left\lfloor \frac{j}{a} \right\rfloor,$$

column:

$$2\times\left\lfloor \frac{i}{a} \right\rfloor;$$

2) level p, row:

$$2\times\left\lfloor \frac{j}{a} \right\rfloor,$$

column:

$$2\times\left\lfloor \frac{i}{a} \right\rfloor+1;$$

3) level p, row:

$$2\times\left\lfloor \frac{j}{a} \right\rfloor+1,$$

column:

$$2\times\left\lfloor \frac{i}{a} \right\rfloor;$$

4) level p, row:

$$2\times\left\lfloor \frac{j}{a} \right\rfloor+1,$$

column:

$$2\times\left\lfloor \frac{i}{a} \right\rfloor+1.$$

When the user scrolls up the mouse, if the current image pyramid is at the top level, the displayed image remains unchanged. Otherwise, the operation is used for carrying out a zooming-out operation, and displaying a corresponding image block of an approximate image an upper level with an area where the mouse is scrolled as a center.

The zooming-out operation includes the following steps: acquiring the row number and column number of the image block where the mouse action position is located in the current level according to the coordinate of the mouse action position of the current level in the image pyramid, and acquiring the row number and column number of the image block corresponding to the upper level through the corresponding relationship between the image block in the current level and the image block in the upper level, so as to obtain the corresponding requested input parameters.

Assuming that the current level is p, the coordinate of the mouse action position is (i,j), and the row number of the corresponding image block is $$\left\lfloor \frac{j}{a} \right\rfloor$$

and the column number thereof is $$\left\lfloor \frac{i}{a} \right\rfloor;$$

if a pair of row number and column number of the corresponding image block in the upper level is $$\left[\left\lfloor \frac{j}{2a} \right\rfloor, \left\lfloor \frac{i}{2a} \right\rfloor\right],$$

the client-side needs to request for the address of the image block from the server-side, and the requested input parameters are level p, row:

column:

$$\left\lfloor \frac{j}{2a} \right\rfloor;$$

$$\left\lfloor \frac{i}{2a} \right\rfloor.$$

When the user performs the translation operation, if the current image pyramid is at an edge or cannot be moved anymore, the displayed image remains changed. Otherwise, the operation is used for continuing the translation operation, and acquiring the image blocks to be displayed as needed, and then splicing and displaying.

The translation operation includes the following steps: a variable S, which is used for marking and storing the requested image blocks, is set, a row range and a column range of the image blocks in the display area at the client are circularly traversed, respectively, and the row number and column number are combined to obtain the parameters of the image block to be requested. In some embodiments, the storage content is the level, row number and column number of the image block. When the image block has been marked by the variable S, there is no need to repeat the request; otherwise, requesting for the image block from the server-side.

Assuming that a current image level is N, a cutting size is a×a, where N and a are positive integers greater than 0; assuming that the approximate image size of the current level is Width×Height, the translation distance of the current image is (tx, ty), and the size of the image display area at the client-side is W×H. A variable S is set to mark and store the requested image block, and the storage content is the level, row number and column number of the image block.

Figure 5:
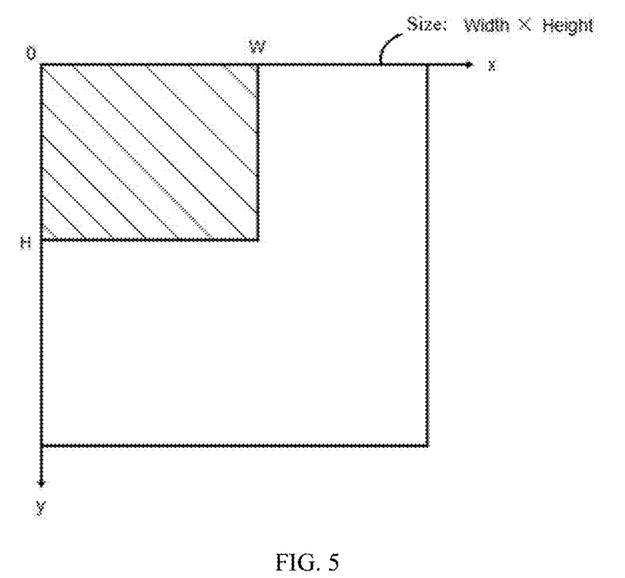
FIG. 5 is a schematic diagram of initializing image display in the client-side image display area according to the present application.
Figure 6:
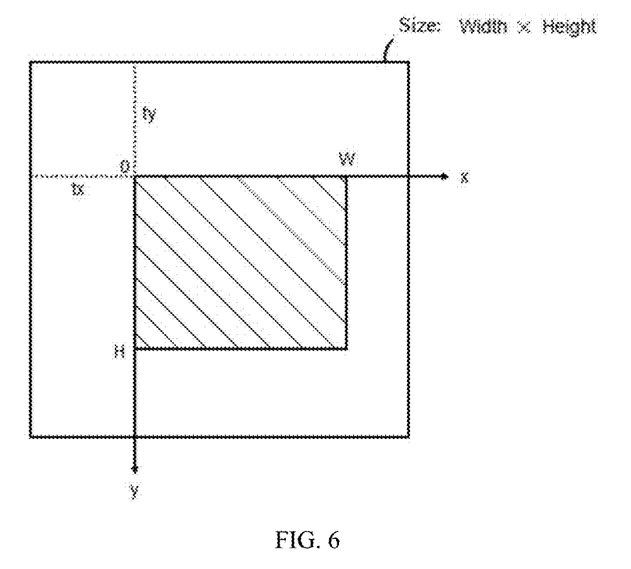
FIG. 6 is a schematic diagram of the image display area at the client-side after image translation according to the present application; a FIG. 7 is a schematic diagram of a method for displaying a high-resolution liver cancer pathological image based on an image pyramid according to the present application.

At an initial stage, the image display area at the client-side is shown in FIG. 5, and the shaded part is the image block displayed to the user. A total size of the image blocks displayed in the image display area at the client-side is the size W×H of the image display area at the client-side; the row range and the column range of the image blocks in the display area are respectively $$0 \sim \left\lfloor \frac{H}{a} \right\rfloor \text{ and } 0 \sim \left\lfloor \frac{W}{a} \right\rfloor;$$

after translation by (tx,ty), the image display area at the client-side is shown in FIG. 6, and the shaded part is the image block displayed to the user; the row range and the column range of the image blocks displayed to the user in the image display area at the client-side are respectively $$\left\lfloor \frac{|ty|}{a} \right\rfloor \sim \left\lfloor \frac{|ty|+H}{a} \right\rfloor \text{ and } \left\lfloor \frac{|tx|}{a} \right\rfloor \sim \left\lfloor \frac{|tx|+W}{a} \right\rfloor.$$

After translation, a row range and a column range of the image blocks in the display area at the client-side are traversed respectively, and the row number and column number are combined to prepare for requesting the corresponding image block. If the image block has been marked by the variable S, there is no need to repeat the request; otherwise, requesting for the image block from the server-side.

In the translation operation, when translated to the right edge, the image cannot be moved to the left any more; when translated the left edge, the image cannot be moved to the right any more; when translated to the upper edge, the image cannot be moved down any more; when translated to the lower edge, the image cannot be moved up any more.

Therefore, the minimum value of tx is 0 and the maximum value is Width-W; The minimum value of ty is 0 and the maximum value is Height-H.

The server-side is used for obtaining information including the size of the original images in each state, the maximum number of levels of the image pyramid, the image block and/or the image cutting size from the data source processing unit and responding to the client-side with the information; and obtaining responded image blocks according to the state of the liver cancer pathological image where the image block is located, the level, the row number and the column number and returning the responded image blocks to the client-side.

Figure 7:
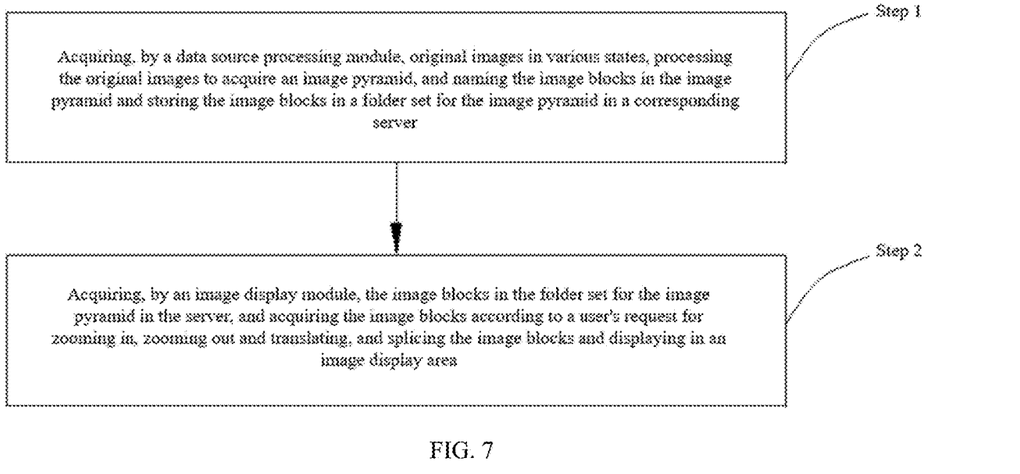

See FIG. 7, A method for displaying a high-resolution liver cancer pathological image based on an image pyramid includes the following steps:

S1, acquiring, by a data source processing module, original images in various states, processing the original images to acquire an image pyramid, and naming the image blocks in the image pyramid and storing the image blocks in a folder set for the image pyramid in a corresponding server;

S2, acquiring, by an image display module, the image blocks in the folder set for the image pyramid in the server, and acquiring the image blocks according to a user's request for zooming in, zooming out and translating, and splicing the image blocks and displaying in an image display area.

Figure 8:
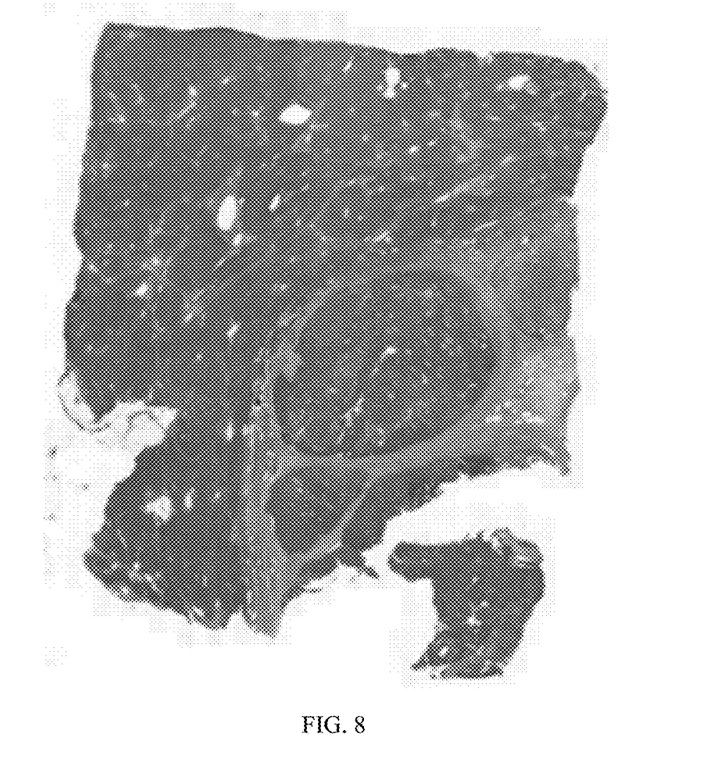
FIG. 8 is a presenting effect diagram of the 7th level image of liver cancer pathology in the original state according to an embodiment.
Figure 9:
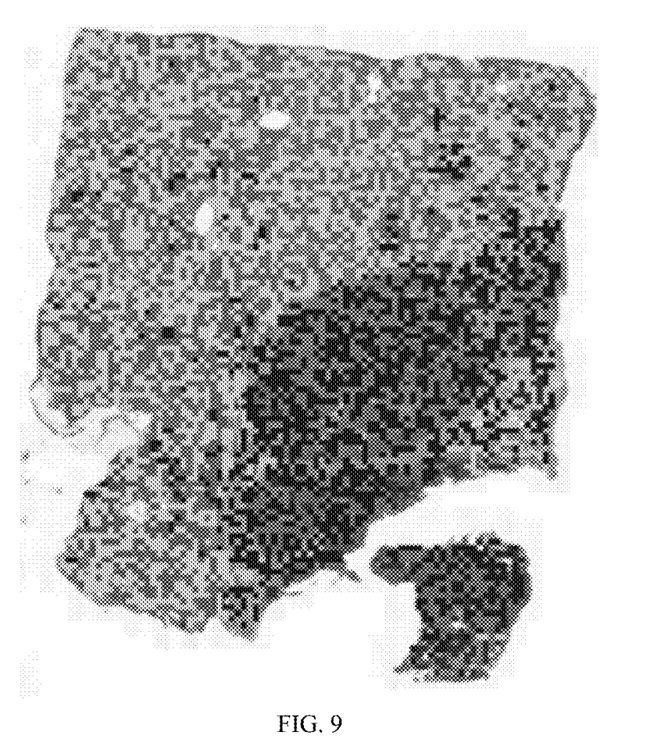
FIG. 9 is a presenting effect diagram of the 7th level image of liver cancer pathology marked with the result of tissue classification according to an embodiment.

Embodiment: Referring to FIG. 8-FIG. 9, the client-side on the Web browser displays two high-resolution pathological images of liver cancer: one is the original pathological image of liver cancer, as shown in FIG. 8; the other is a pathological image of liver cancer marked with the result of tissue classification, as shown in FIG. 9.

The original sizes of the pathological images of liver cancer in these two states are both 57024×134208, and the image type is png. The rendering process is as follows:

1) The data source processing module calculates the maximum number of levels and image cutting size of the image pyramid, and the maximum number of levels of the image pyramid is 7, and the image cutting size is 446×446.

The image sizes of each level are as follows: the $0^{th}$ level 57024×134208, the $1^{st}$ level 28512×67104, the $2^{nd}$ level 14256×33552, the $3^{rd}$ level 7128×16776, the $4^{th}$ level 3564×8388, the $5^{th}$ level 1782×4194, the $6^{th}$ level 891×2097, and the $7^{th}$ level 446×1049.

2) Through the image naming and storage by the image block processing unit, each level of the liver cancer pathological image in each state is named and stored in the target storage space specially opened for the image pyramid on the server according to the state, level, row number and column number of the image block.

3) In the image display module, as shown in FIG. 8, the top level of the original state, namely the $7^{th}$ level image, is initially displayed. The size of the $7^{th}$ level image is 446×1049, which is composed of three image blocks: two 446×446 image blocks and one 446×157 image block.

Figure 10:
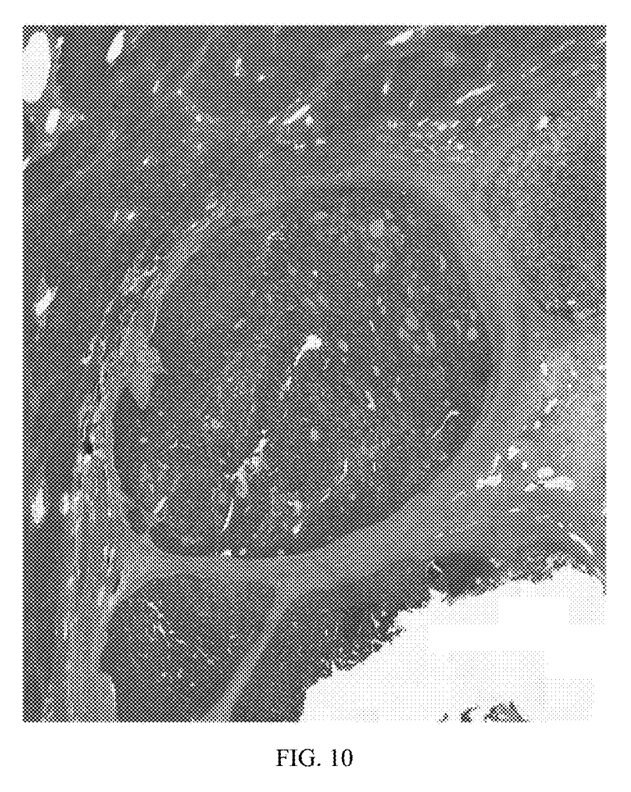
FIG. 10 is a presenting effect diagram of part of the 5th level image of liver cancer pathology in the original state according to an embodiment.

4) The client-side in the image display module monitors the user's mouse operation. FIG. 10 shows six image blocks in the $2^{nd}$ row, the $1^{st}$ column, the $2^{nd}$ row, the $2^{nd}$ column, the $3^{rd}$ row, the $2^{nd}$ column, the $4^{th}$ row, the 1$^{st}$ column and the 4$^{th}$ row, the 2$^{nd}$ column of the 5$^{th}$ level approximate image displayed after the user clicks the mouse twice and performs translation operation.

Figure 11:
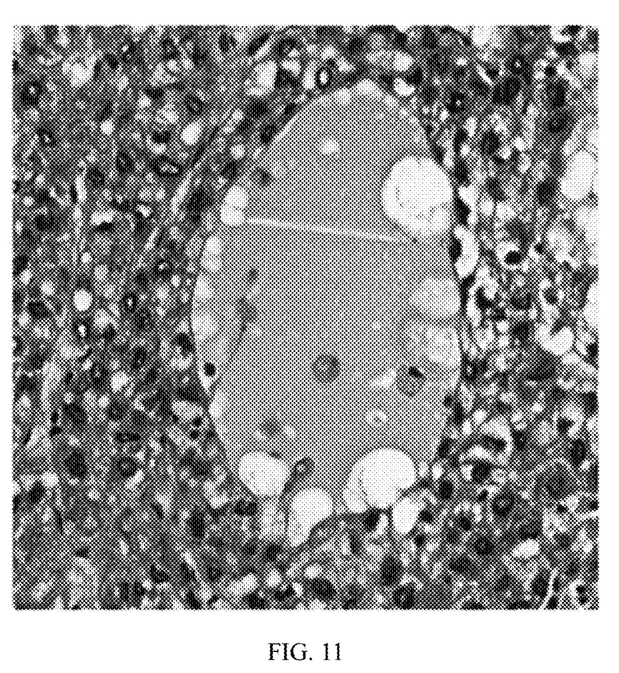
FIG. 11 is a presenting effect diagram of part of the 5th level image of liver cancer pathology in the original state according to an embodiment.

5) FIG. 11 shows four image blocks of the original image in the 98$^{th}$ row, 67$^{th}$ column, 99$^{th}$ row, 67$^{th}$ column and 99$^{th}$ row, 68$^{th}$ column of the 0$^{th}$ level after the user clicks the mouse five times again and performs the translation operation.

Finally, this pathological image of liver cancer with the size of 57024×134208 and the image type of png is rendered and displayed by the OpenSeadragon and the method of the present application respectively, and the waiting time of users is as follows:

1) Image blocks are acquired synchronously based on OpenSeadragon, and the average time for users to wait for the first screen display is 12350 ms; from the enlarged picture of the bottom original image to the top approximate image, the average time for users to wait for image display is 5972 ms;
2) The image block is acquired through the asynchronous mode of the present application, and the average waiting time of the user for the first screen display is 1511 ms; from the enlarged picture of the bottom original image to the top approximate image, the average time for users to wait for image display is 3500 ms.

By adopting the method of the present application, the time for users to wait for the first screen display is reduced by 87.8%; from the enlarged picture of the bottom original image to the top approximate image, the user's waiting time for image display is reduced by 41.4%.

What has been described above is only the preferred embodiment of the present application, and it is not used to limit the present application. For those skilled in the art, the present application may have various modifications and changes. Any modification, equivalent substitution, improvement, etc. made within the spirit and principle of the present application shall be included in the protection scope of the present application.

What is claimed is:

1. A system for displaying a high-resolution liver cancer pathological image based on an image pyramid, comprising:
    a data source processing module configured for acquiring original images in various states, processing the original images, acquiring an image pyramid, naming image blocks in the image pyramid and storing the image blocks in a folder set for the image pyramid in a corresponding server;
    wherein the data source processing module comprises:
    a data source processing unit configured for acquiring the original images in various states from an original image database, setting a size threshold, calculating a size of the original images, calculating a maximum number of levels of the image pyramid according to the size threshold and the size of the original images, and calculating an image cutting size from the maximum number of levels of the image pyramid;
    wherein a process of the data source processing unit is as follows:
    the original images in various states are acquired from an original image database, the size, comprising a width of the original images and a height of the original images, of the original images is calculated, and the size threshold is set;
    when the size threshold is 500×500, the width of the original images is Width, the height is Height, and the maximum number of levels of the image pyramid is N;
    the images are continuously downsampled until the width reaches the size threshold, and accordingly a number of times of downsampling i shall satisfy $$\frac{\text{Width}}{2^i} \le 500, i \in N; i \ge \log_2 \frac{\text{Width}}{500}, i \in N,$$

is calculated, and a minimum value that meets the condition is taken to obtain the number of times of downsampling, which is the maximum number of levels of the image pyramid, and then the calculated i is substituted into $$\left\lceil \frac{\text{Width}}{2^i} \right\rceil$$

to obtain the image cutting size $$\left\lceil \frac{\text{Width}}{2^i} \right\rceil \times \left\lceil \frac{\text{Width}}{2^i} \right\rceil;$$

when the width of the original images is less than or equal to the height of the original images, the original images are downsampled until the width of the original images reaches the size threshold, the downsampling is stopped, the number of times of downsampling is calculated, which is the maximum number of levels of the corresponding image pyramid, and the image cutting size is calculated from the number of times of downsampling;
    when the width of the original images is larger than the height of the original images, the original images are downsampled until the height of the original images reaches the size threshold, the downsampling is stopped, the number of times of downsampling is calculated, which is the maximum number of levels of the corresponding image pyramid, and the image cutting size is calculated from the number of times of downsampling;
    an image block processing unit configured for preprocessing the original images and cutting the preprocessed original images according to the image cutting size to obtain a plurality of image blocks, wherein each level of the image blocks together forms an image pyramid, and each image block is named and stored in the folder set for the image pyramid in the corresponding server;
    wherein a process of the image block processing unit is as follows:
    step S1, performing Gaussian blur processing on the original image as a target image to obtain a filtered image subjected to Gaussian blur;
    step S2, downsampling the filtered image to obtain an approximate image;
    step S3, cutting the target image according to the image cutting size to obtain a plurality of image blocks;
    step S4, each level of the image blocks forming an image pyramid together, naming each image block and storing each image block in the folder set for the image pyramid in the corresponding server;
    step S5, when a width of the approximate image is larger than a width of the image cutting size, taking the approximate image as the target image in step S1 and traversing step S1 to step S5; otherwise, cutting a last approximate image obtained in step S2 according to the image cutting size, naming each cut image block and stored each cut image block in the folder set for the image pyramid in the corresponding server;

wherein each image block in the image block processing unit is named as n_m according to a character string obtained by splicing a row number n and a column number m in the image pyramid with an underline, and the image block is stored in the folder set for the image pyramid in the corresponding server;

an image display module configured for acquiring the image blocks in the folder set for the image pyramid in the server, zooming in, zooming out and translating the image blocks according to a user's request, and splicing the image blocks and displaying the image blocks in an image display area;

wherein the image display module comprises:

a client-side configured for initiating a request for obtaining basic information of an image to a server-side, and simultaneously monitoring user mouse events, asynchronously requesting image blocks to be loaded to the server-side according to a user's operation, requested input parameters being a state of the liver cancer pathological image where the image blocks to be obtained are located, a level where the image blocks are located, a row number and a column number, and splicing the obtained image blocks and displaying in the image display area of a browser;

wherein monitoring of user mouse events comprises:

an operation of clicking mouse or scrolling down mouse by a user: the operation is used for keeping the displayed image skill if the current image pyramid is at the bottom when the user clicks the mouse or scrolls down the mouse; otherwise, the operation is used for carrying out a zooming-in operation, and displaying a corresponding image block of an approximate image in a lower level with an area, as a center, where the mouse is clicked or scrolled;

wherein the zooming-in operation comprises the following steps: obtaining the row number and column number of the image block where a mouse action position is located in a current level according to a coordinate of the mouse action position of the current level in the image pyramid, and obtaining the row number and column number of the corresponding image block in a lower level through the corresponding relationship between the image block in the current level and the image block in the lower level, so as to obtain the corresponding requested input parameters;

the current level is p, the coordinate of the mouse action position is (i,j), and the row of the corresponding image block is $$\left\lfloor \frac{j}{a} \right\rfloor,$$

and the column thereof is $$\left\lfloor \frac{i}{a} \right\rfloor;$$

there are four image blocks corresponding to the lower level, and pairs of the row number and column number thereof are $$\left[2\times\left\lfloor \frac{j}{a} \right\rfloor, 2\times\left\lfloor \frac{i}{a} \right\rfloor\right], \left[2\times\left\lfloor \frac{j}{a} \right\rfloor, 2\times\left\lfloor \frac{i}{a} \right\rfloor+1\right], \left[2\times\left\lfloor \frac{j}{a} \right\rfloor+1, 2\times\left\lfloor \frac{i}{a} \right\rfloor\right] \text{ and } \left[2\times\left\lfloor \frac{j}{a} \right\rfloor+1, 2\times\left\lfloor \frac{i}{a} \right\rfloor+1\right]$$

respectively, then the client-side needs to request for the addresses of these four image blocks from the server-side, and the requested input parameters are:

1) Level p, row:

$$2\times\left\lfloor \frac{j}{a} \right\rfloor,$$

column:

$$2\times\left\lfloor \frac{i}{a} \right\rfloor;$$

2) level p, row:

$$2\times\left\lfloor \frac{j}{a} \right\rfloor,$$

column:

$$2\times\left\lfloor \frac{i}{a} \right\rfloor+1;$$

3) level p, row:

$$2\times\left\lfloor \frac{j}{a} \right\rfloor+1,$$

column:

$$2\times\left\lfloor \frac{i}{a} \right\rfloor;$$

4) level p, row:

$$2\times\left\lfloor \frac{j}{a} \right\rfloor+1,$$

column:

$$2\times\left\lfloor \frac{i}{a} \right\rfloor+1;$$

an operation of upward scrolling mouse by a user: the operation is used for keeping the displayed image skill if the current image pyramid is at a top level when the user scrolls the mouse upward; otherwise, the operation is used for carrying out a zooming-out operation, and displaying a corresponding image block of an approximate image an upper level with an area where the mouse is scrolled as a center;

the zooming-out operation comprises the following steps:
acquiring the row number and column number of the image block where the mouse action position is located in the current level according to the coordinate of the mouse action position of the current level in the image pyramid, and acquiring the row number and column number of the image block corresponding to the upper level through the corresponding relationship between the image block in the current level and the image block in the upper level, so as to obtain the corresponding requested input parameters;

the current level is p, the coordinate of the mouse action position is (i,j), and the row number of the corresponding image block is $$\left\lfloor \frac{j}{a} \right\rfloor$$

and the column number thereof is $$\left\lfloor \frac{i}{a} \right\rfloor;$$

if a pair of row number and column number of the corresponding image block is in the upper level is $$\left[\left\lfloor \frac{j}{2a} \right\rfloor, \left\lfloor \frac{i}{2a} \right\rfloor\right],$$

the client-side needs to request for the address of the image block from the server-side, and the requested input parameters are level p, row:

$$\left\lfloor \frac{j}{2a} \right\rfloor;$$

column:

$$\left\lfloor \frac{i}{2a} \right\rfloor;$$

a translation operation by a user: the operation is used for keeping the displayed image still if the current image pyramid is on an edge or can no longer move; otherwise, the operation is used for continuing the translation operation, and acquiring the image blocks to be displayed as needed, and then splicing and displaying; wherein the translation operation comprises the following steps: setting a variable S, which is used for marking and storing the requested image blocks, wherein the storage content is the level, row number and column number of the image block; circularly traversing a row range and a column range of the image blocks in the display area at the client-side, respectively, and combining the row number and column number to obtain the parameters of the image block to be requested, wherein when the image block has been marked by the variable S, there is no need to repeat the request; otherwise, requesting for the image block from the server-side;

a cutting size is a×a, wherein a is a positive integer greater than 0; a translation distance of the current image is (tx,ty), and the size of the image display area at the client-side is W×H; at an initial stage, a total size of the image blocks displayed in the image display area at the client-side is the size W×H of the image display area at the client-side; the row range and the column range of the image blocks in the display area are respectively $$0 \sim \left\lfloor \frac{H}{a} \right\rfloor \text{ and } 0 \sim \left\lfloor \frac{W}{a} \right\rfloor;$$

after translation by (tx,ty), the row range and the column range of the image blocks displayed to the user in the image display area at the client-side are respectively $$\left\lfloor \frac{|ty|}{a} \right\rfloor \sim \left\lfloor \frac{|ty|+H}{a} \right\rfloor \text{ and } \left\lfloor \frac{|tx|}{a} \right\rfloor \sim \left\lfloor \frac{|tx|+W}{a} \right\rfloor;$$

the server-side configured for obtaining information comprising the size of the original images in each state, the maximum number of levels of the image pyramid, the image block and/or the image cutting size from the data source processing unit and responding to the client-side with the information; and obtaining responded image blocks according to the state of the liver cancer pathological image where the image block is located, the level, the row number and the column number and returning the responded image blocks to the client-side.

2. The system for displaying a high-resolution liver cancer pathological image based on an image pyramid according to claim 1, wherein in the translation operation, when translated to the right edge, the image cannot be moved to the left any more; when translated the left edge, the image cannot be moved to the right any more; when translated to the upper edge, the image cannot be moved down any more; when translated to the lower edge, the image cannot be moved up any more.

3. A method for displaying a high-resolution liver cancer pathological image based on an image pyramid, using the system according to claim 1, comprising steps of:

S101, acquiring, by a data source processing module, original images in various states, processing the original images to acquire an image pyramid, and naming the image blocks in the image pyramid and storing the image blocks in a folder set for the image pyramid in a corresponding server;

S102, acquiring, by an image display module, the image blocks in the folder set for the image pyramid in the server, and acquiring the image blocks according to a user's request for zooming in, zooming out and translating, and splicing the image blocks and displaying in an image display area.

* * * * *